(12) United States Patent
Gao et al.

(10) Patent No.: US 6,900,305 B2
(45) Date of Patent: May 31, 2005

(54) ISOLATED YEAST PROMOTER SEQUENCE AND A METHOD OF REGULATED HETEROLOGOUS EXPRESSION

(75) Inventors: Johnway Gao, Richland, WA (US); Rodney S. Skeen, Pendleton, OR (US); Brian S. Hooker, Kennewick, WA (US); Daniel B. Anderson, Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 265 days.

(21) Appl. No.: 09/921,944

(22) Filed: Aug. 2, 2001

(65) Prior Publication Data

US 2002/0155549 A1 Oct. 24, 2002

Related U.S. Application Data

(63) Continuation-in-part of application No. 09/632,314, filed on Aug. 4, 2000, now abandoned.

(51) Int. Cl.$^7$ .......................... C12P 21/06; C12N 5/00; C07H 21/02; C07H 21/04
(52) U.S. Cl. ..................... 536/24.1; 536/23.1; 435/325; 435/69.1
(58) Field of Search ............................ 536/24.1, 23.1; 435/325, 69.1, 70.1, 455, 465; 800/278

(56) References Cited

U.S. PATENT DOCUMENTS

| | | | |
|---|---|---|---|
| 4,676,986 A | | 6/1987 | Sills et al. |
| 5,100,794 A | | 3/1992 | Strasser et al. |
| 6,465,635 B1 | * | 10/2002 | Gao et al. .................. 536/24.1 |
| 6,528,636 B1 | * | 3/2003 | Gao et al. .................. 536/24.1 |
| 6,551,798 B2 | * | 4/2003 | Gao et al. .................. 435/69.1 |

FOREIGN PATENT DOCUMENTS

| | | |
|---|---|---|
| EP | 0260404 A2 | 3/1988 |
| WO | PCT/US01/24476 | 6/2002 |

OTHER PUBLICATIONS

AM Sills et al., "Production of Amylolytic Enzymes by Several Yeast Species", p. 313–316. 1982.
T Hongpattarakere et al., "Optimization of Single–Cell–Protein Production From Cassava Starch Using *Schwanniomyces Castellii*", p. 607–609. 1995.
SA Lemmel et al., "Kinetics of Growth and Amylast Production of *Saccharomycopsis Fibuligera* on Potato Processing Wastewater", p. 387–393. 1980.
K Kim et al., "High–Efficiency, One–Step Starch Utilization by Transformed *Saccharomyces* Cells Which Secrete Both Yeast Glucoamylase and Mouse a–Amylase", p. 966–971. 1988.

C Laluce et al., "New Amylolytic Yeast Strains for Starch and Dextrin Fermentation", p. 2447–2451. 1988.
IH Evans, "Yeast Protocols", p. 103–107. 1996.
K Pirselova et al., "Fermentation of Starch to Ethanol by a Co–Culture of *Saccharomycopsis Fibuligera* and *Saccharomyces Cerevisiae*", p. 338–341. 1993.
YW Ryu et al., Direct Alcohol Fermentation of Starch by a Derepressed Mutant of *Schwanniomyces Castellii*. p. 107–112. 1994.
K Sreekrishna et al., "High–Level Expression, Purification, and Characterization of Recombinant Human Tumor Necrosis Factor Synthesized in the Methlotropphic Yeast *Pichia Pastoris*". p. 4117–4125. 1989.
JM Cregg et al., "Recent Advances in the Expression of Foreign Genes in *Pichia Patoris*", p. 905–909. 1993.
D Porro et al., "Replacement of a Metabolic Pathway for Large–Scale Production of Lactic Acid From Engineered Yeasts". p. 4211–4215. 1999.
NWY Ho. "Successful Development of Hazard–Free, User–Friendly. Genetically Engineered Microorganisms for Effective Production of Environmentally Friendly Chemicals from Renewable Biomass", p. 77–78. 1999.
TT Wang, et al., "The Molecular Biology of *Schwanniomyces Occidentalis* Klocker", p. 113–143. 1999.
TM Downhanick et al., "Expression and Regulation of Glucoamylase From the Yeast *Schwanniomyces Castellii*". p. 2360–2366. 1990.
RJ Dohmen et al., "Cloning of the *Schwanniomyces Occidentalis* Glucoamylase Gene (GAMI) and its expression in *Saccharomyces Cerevisiae*". p. 111–121. 1990.
RJ Dohmen et al., "GUS Fusions: B–Glucuronidase as a Sensitive and Versatile Gene Fusion Marker in Higher Plants", p. 3901–3907. 1987.
JR Dohmen et al., Locus Accession No. M60207, Apr. 1993.
Strasser et al., "Analysis of the α–amylase gene of *Schwanniomyces occidentalis* and the secretion of its gene product in transformants of different yeast genera" Eur. J. Biochem., vol. 184, Apr./Jul. 1989. pp. 699–706.
Sills et al., "Isolation and Characterization of the Amylotic System of *Schwanniomyces castellii*". J. Inst. Brew., Sept.–Oct. 1984. vol. 90. pp. 311–314.

* cited by examiner

*Primary Examiner*—Joseph Woitach
(74) *Attorney, Agent, or Firm*—Wells St. John P.S.

(57) ABSTRACT

The present invention provides the promoter clone discovery of a glucoamylase gene of a starch utilizing yeast strain *Schwanniomyces castellii*. The isolated glucoamylase promoter is an inducible promoter, which can regulate strong gene expression in starch culture medium.

16 Claims, 7 Drawing Sheets

```
   1   tgatcatcttgaagttaaatccaagttattcaagtaatttaaagttgaataatgtagtta   60
  61   tttcagtggccttaaaccagtccatcgagacgacttcagcctcttcgagaccacaaggtt  120
 121   cgtttaataaggaaatgaatagaatcacctggagatattcgcagccattaatactatcaa  180
 181   gtgaaaatcctgaagaaaaattaattgcaagattttttgactaatagtaaaggtagtgaac 240
 241   atgaaagtggtattcaagttaaattttttgattaatgatcctccactgaaattttctaagg 300
 301   ctttatattttgatgatgaatcaacagaggttccttgtgtaaggaatcttattagtggaa  360
 361   gctacagcagtcattcttaaacatgattaatgtctagatttattggttatttaggcattc  420
 421   ttttttttaaaatattttttgttaatatctttgagtttatgttttttgttcgttttatct  480
 481   tttaaagtagtgtttatagttttagtattgttaaccttttttttcctaaatgttagtatgc  540
 541   atgcttaaaatgatgtcagaggtagagtatgaattaattccttttataaatgctgttttg  600
 601   tgagatcttttaaaattatctatctttctctttaaaggatatgttttgatttctgattga  660
 661   tttgagttccaacgacaatcgaatgtattcatatagtagttactaccttaaacacaatcc  720
 721   agatggtttaaccaactgatgcctaagtttcatgtggtgctctttaacatccttttttgtc  780
 781   ttcaaatttcaatgccattagttcacatgtatatacgccaagagagtttgtgaccaact  840
 841   tacatttactagcaagtattatctacaaagcaaaaattacgacatatttgtgttggatcc  900
 901   atcaactgtggacacgaataacaagttcccaggattcctaattattcaactgccagataa  960
 961   ataacatatatccaaaggttcaacattatttaccaaattcaaagttggattttgttaaat 1020
1021   ggaatgacaatagaaattggttgggtttatgtgcaaaagaatctaattttgcatatattt 1080
1081   tcgtaaacttcaattcctaaaatcttgcgaaacttctctttagaggaaattggttccatt 1140
1141   ctaccttctatcaaactactccaaatacaagcggcttaaaatctacatgtaaataccta 1200
1201   ctgttacaattattctcccttgaattgaccaacctgaccatgaaacctttttggaatcag 1260
1261   cctatttacactaataatttttatcctaagtgccatggaagctattatataagttttacc 1320
1321   agtgagagaggatcttgacttgacgaacaacatttcaactagaatgctctatatcttcct 1380
1381   ccgggaaaagcggccgctaccatttgttttacactctcaccatcacaaaagtgccattca 1440
1441   acggattttgtccgcgatctctcggtaaaatgtgttctcgaaatgtgccttattgccaa  1500
1501   aaaataaaaataaaaaataatgtgggggtggcatccttcaacttgtcggatttattgcg  1560
1561   taatagatttcaatcaacatgatcttaatccatactggcttatgctctcttagaggctta  1620
1621   tctcttaataatttttattatatatctattctaactattgaaaaactattgaatatgcttt 1680
```

FIG. 4

```
1681  aaaactggctatgctgtatttgacttctcaatgcaaaattcaacacttctataatgtaac 1740
1741  acactaaaaattttttcagaatcggaatagtcgagacaattgattttccgaactattgcga 1800
1801  aatccaatggagcaacaatgagagatctacattttaaaccccagtctactccagatattg 1860
1861  gagtataaccccattcttaccgttatatccatgacccgcatcgaaattttcaaaggattt 1920
1921  cgaggaaattctttcctaaaatacgaagtgttattggtgattcaattactacggaaacta 1980
1981  ctccattatggatgtagagttggtgaatgtagcgcaattgtaatttgcgaagttatagta 2040
2041  atagtttggcaaactggagaatttttcattattgggaaaatataaataaaggcaagtatc 2100
2101  cattgaaattttaaaaatgaactcatgactgtattataacaagcaagATGattttctga 2160
2160  agctgattaaaagtatagtaat                                       2182
```

FIG. 4 (Continued)

```
GAM77: 1823 agatctacattttaaaccccagtctactccagatattggagtataacccattcttaccg 1882
            ||||||||||||||||||||||||||||||||||||||||||||||||||||||||||||
GAM76:    1 agatctacattttaaaccccagtctactccagatattggagtataacccattcttaccg   60

GAM77: 1883 ttatatccatgacccgcatcgaaattttcaaaggatttcgaggaaattctttcctaaaat 1942
            ||||||||||||||||||||||||||||||||||||||||||||||||||||||||||||
GAM76:   61 ttatatccatgacccgcatcgaaattttcaaaggatttcgaggaaattctttcctaaaat  120

GAM77: 1943 acgaagtgttattggtgattcaattactacggaaactactccattatggatgtagagttg 2002
            |||||||||||||||||||||||||||||||||||||||||||||    |||||  |||||||||
GAM76:  121 acgaagtgttattggtgattcaattactacggaaactactc--atatggtagtagagttg  178

GAM77: 2003 gtgaatgtagcgcaattgtaatttgcgaagttatagtaatagtttggcaaactggagaat 2062
            ||||||||||||||||||||||||||||||||||||||||||||||||||||||||||||
GAM76:  179 gtgaatgtagcgcaattgtaatttgcgaagttatagtaatagtttggcaaactggagaat  238

GAM77: 2063 ttttcattattgggaaaatataaataaaggcaagtatccattgaaattttaaaaatgaac 2122
            |||||||||||||||||||||||||||||||||||||||||||||||||||| |||||||
GAM76:  239 ttttcattattgggaaaatataaataaaggcaagtatccattgaaatttt-aaaatgaac  297

GAM77: 2123 tcatgactgtattataacaagcaagATG 2150
            ||||||||||||||||||||||||||||
GAM76:  298 tcatgactgtattataacaagcaagATG  325
```

FIG. 5

ISOLATED YEAST PROMOTER SEQUENCE AND A METHOD OF REGULATED HETEROLOGOUS EXPRESSION

This application is a continuation-in-part of application Ser. No. 09/632,314 filed Aug. 4, 2000 now abandoned.

The U.S. Government has a paid-up license in this invention and the right in limited circumstances to require the patent owner to license others on reasonable terms as provided for by the terms of Contract DE-AC0676RLO1830 awarded by the U.S. Department of Energy.

FIELD OF THE INVENTION

The present invention relates specifically to the isolation of a yeast gene regulatory sequence (promoter), which is native to Schwanniomyces castellii (ATTCC 26077) and can regulate gene expression in a heterologous yeast host using starch as the sole carbon source. More specifically, the starch can be used as an inducing agent for the expression of native or foreign genes, which are fused to the isolated yeast promoter. The transformed host cells bearing the promoter-gene fusion can grow in culture medium containing various carbon sources, and the gene expression is induced by starch addition as a gene expression inducing-agent. The heterologous host is preferably bacteria, yeast, mold, plant cell, plant tissue and whole plant.

DESCRIPTION OF THE RELATED ART

Natural yeast strains have been identified that can use starch as a primary growth substrate via complete or partial enzymatic hydrolysis. These yeast strains include but not limit to Saccharomycopsis fibuligera, Schwanniomyces castellii, and Saccharomyces diastaticus, which can produce and secrete both alpha-amylase and glucoamylase to liquefy and hydrolyze starch into glucose. A fusion yeast cell strain of Saccharomyces diastaticus and Saccharomyces cerevisiae could degrade 60% of starch present in culture media within two days. In addition, other natural Saccharomyces species can ferment starch and dextrin to ethanol, as well as improve ethanol production from starch and higher sugars.

The ability to genetically modify yeast strains has greatly advanced both protein expression engineering and metabolic engineering for the past two decades. The use of yeast for producing transgenic prokaryotic and eukaryotic heterologous proteins has the added advantage that yeast and filamentous mold are microbial eukaryotes and they are more closely related to animal cells. Hence, yeasts possess the molecular genetic manipulation and growth characteristics of prokaryotic organisms together with the subcellular machinery for performing eukaryotic post-translational protein modification. For example, Pichia pastoris is able to synthesize functional recombinant protein and its glycosylation abilities are very similar to those of animal cells, though the glycosylation in another yeast strain, Saccharomyces cerevisiae is different from that of an animal. In addition, the metabolic pathway of a regular ethanol producing yeast strain can be genetically altered to accumulate large amount of lactic acid, and to increase xylose utilization rate. However, only a few yeast systems (transformation vector and promoters) are available for protein engineering and metabolic engineering, which include Saccharomyces cerevisiae, Pichia pastoris, among others.

Starch utilizing yeast strain, Schwanniomyces castellii or Schwanniomyces occidentalis, is one of the most important microorganisms since it can directly use starch as its growth medium. Due to the low level of glycosylation and the ability of protein secretion, Schwanniomyces castellii is a promising host for heterologous protein expression. However, the molecular study of Schwanniomyces sp. is very limited. Only about 21 genes have been cloned and very few promoter sequences have been cloned and characterized in their full length from Schwanniomyces sp. The ability to genetically manipulate Schwanniomyces sp. depends on the successfulness in developing the transformation methods and gene expression systems. To effectively direct the transcription or expression of an interested gene, strong gene regulating elements or promoters are required. These promoters can be isolated from the upstream sequences of strongly expressed gene clones.

Glucoamylase, a 146-kDa protein, is one of the highly expressed clones in Schwanniomyces castellii, and different carbohydrates such as maltose and starch regulate its expression. The expression level of glucoamylase can be increased by 100-fold when the cells are shifted from glucose culture medium to maltose culture medium. The gene regulatory element (promoter) of the glucoamylase gene would be a useful genetic element to be used for the regulation of foreign gene expression. However, the Schwanniomyces castellii glucoamylase promoter has never been fully sequenced and characterized. To genetically manipulate Schwanniomyces sp, either for the purpose of metabolic pathway modification, conferring necessary traits such as chemical production, or producing biocatalyst of interest, high levels of mRNA expression are always desirable. Therefore, there is a need to isolate strong promoter sequences of Schwanniomyces sp. and characterize its function.

The following references disclose technical information useful in this art:

Sills A M, Stewart G G. 1982. Production of amylolytic enzymes by several yeast species. J. Inst. Brew. 88: 313–316.

Hongpattarakere T, H-Kittikun A. 1995. Optimization of single-cell-protein production from cassava starch using Schwanniomyces castellii. J. Microbiol. Biotechnol. 11: 607–609.

Lemmel S A, Heimsch R C, Korus R A. 1980. Kinetics of growth and amylase production of Saccharomycopsis fibuligera on potato processing. Appl. Environ. Microbiol. 39: 387–393.

Kim K, Park C S, Mattoon J R. 1988. High-efficiency one-step starch utilization by transformed Saccharomyces cells which secrete both yeast glucoamylase and mouse alpha amylase. Appl. Environ. Microbiol. 54: 966–971.

Laluce C, Bertolini M C, Ernandes J R, Martini A V, Martini A. 1988. New amylolytic yeast strains for starch and dextrin fermentation. Appl. Environ. Microbiol. 54: 2447–2451.

Pirselova K, Smogrovicova D. Balaz S. 1993. Fermentation of starch to ethanol by a co-culture of Saccharomycopsis fibuligera and Saccharomyces cerevisiae. World J. Microbiol. Biotechnol. 9: 338–341.

Ryu Y W, Ko S H, Byun S Y, Kim C. 1994. Direct alcohol fermentation of starch by a derepressed mutant of Schwanniomyces castellii. Biotechnol. Lett. 16:107–112.

Sreekrishna K, Nelles L, Potenz R, Cruze J, Mazzaferro P, Fish W, Fuke M, Holden K, Phelps D, Wood P, Parker K. 1989. High-level expression, purification, and characterization of recombinant human tumor necrosis factor synthesized in the methylotrophic yeast Pichia pastoris. Biochemistry 28: 4117–4125.

Cregg J M, Vedvick T S, Raschke W C. 1993. Recent advances in the expression of foreign genes in Pichia pastoris. Biotechnol. 11: 905–910.

Porro D, Bianchi M M, Brambilla L, Menghini R, Bolzani D, Carrera V, Lievense J, Liu C L, Ranzi B M, Frontali L, Alberghina L. 1999. Replacement of a metabolic pathway for large-scale production of lactic acid from engineered yeasts. Appl. Environ. Microbiol. 65(9): 4211–4215.

Ho N W Y. 1999. Successful development of hazard-free, user-friendly genetically engineered microorganisms for effective production of environmentally friendly chemicals from renewable biomass. Proceedings of 3$^{rd}$ Annual Green Chemistry and Engineering Conference, Washington, D.C. Pp. 77–78.

Wang T T, Lee C F, Lee B H. 1999. The molecular biology of *Schwanniomyces occidentalis* Klocker. Critical Review in Biotechnol. 19(2): 113–143.

Jefferson R A, Kavanagh T A, Bevan M W. 1987. GUS fusions: beta-glucuronidase as a sensitive and versatile gene fusion marker in higher plants. *EMBO J.* 6 (13): 3901–3907.

Dohmen R J, Strasser A W M, Martens F B, Dahlems U M, Hollenberg C P. 1990. Cloning of the *Schwanniomyces occidentalis* glucoamylase gene (GAM1) and its expression in *Saccharomyces cerevisiae*. Gene 95: 111–121.

Strasser A, Martens F B, Dohnen J, Hollenberg C P. 1992. Amylolytic enzymes producing microorganisms, constructed by recombinant DNA technology and their use for fermentation processes. U.S. Pat. No. 5,100,794.

Claros M G, Abarca D, Fernandez-Lobato M, Jimenez A. 1993. Molecular structure of the SWA2 gene encoding an AMY1-related alph-amylase from *Schwanniomyces occidentalis*. Curr. Genet. 24: 75–83.

Piper P. 1996. Isolation of yeast DNA, Methods in Molecular Biology, 53:103–107.

SUMMARY OF THE INVENTION

The present invention provides the promoter clone discovery of a glucoamylase gene of a starch utilizing yeast strain *Schwanniomyces castellii*. The isolated glucoamylase promoter is an inducible promoter, which can regulate strong gene expression in starch culture medium.

An object of the present invention is to provide an isolated yeast promoter, which is native to *Schwanniomyces castellii* (ATCC 26077) and located upstream of and in control of a glucoamylase gene.

Another object of the invention is to provide an isolated yeast promoter that has a sequence of 1662 base pairs prior to the initiation codon of glucoamylase gene.

Yet another object of the invention is to provide a strong gene promoter that allows effective direction of transcription or expression of a gene of interest.

Another object of the invention is to provide a process of expressing a gene of interest in bacterial, yeast, mold, and plant/plant cell species.

BRIEF DESCRIPTION OF THE DRAWINGS

FIG. 4 is the sequence of *S. castellii* glucoamylase promoter; SEQ ID NO:8.

FIG. 5 is the sequence comparison of two *S. castellii* glucoamylase promoter sequences; SEQ ID NO:9 (top sequence) and SEQ ID NO:10 (bottom sequence).

DETAILED DESCRIPTION OF THE INVENTION

Figure 1:
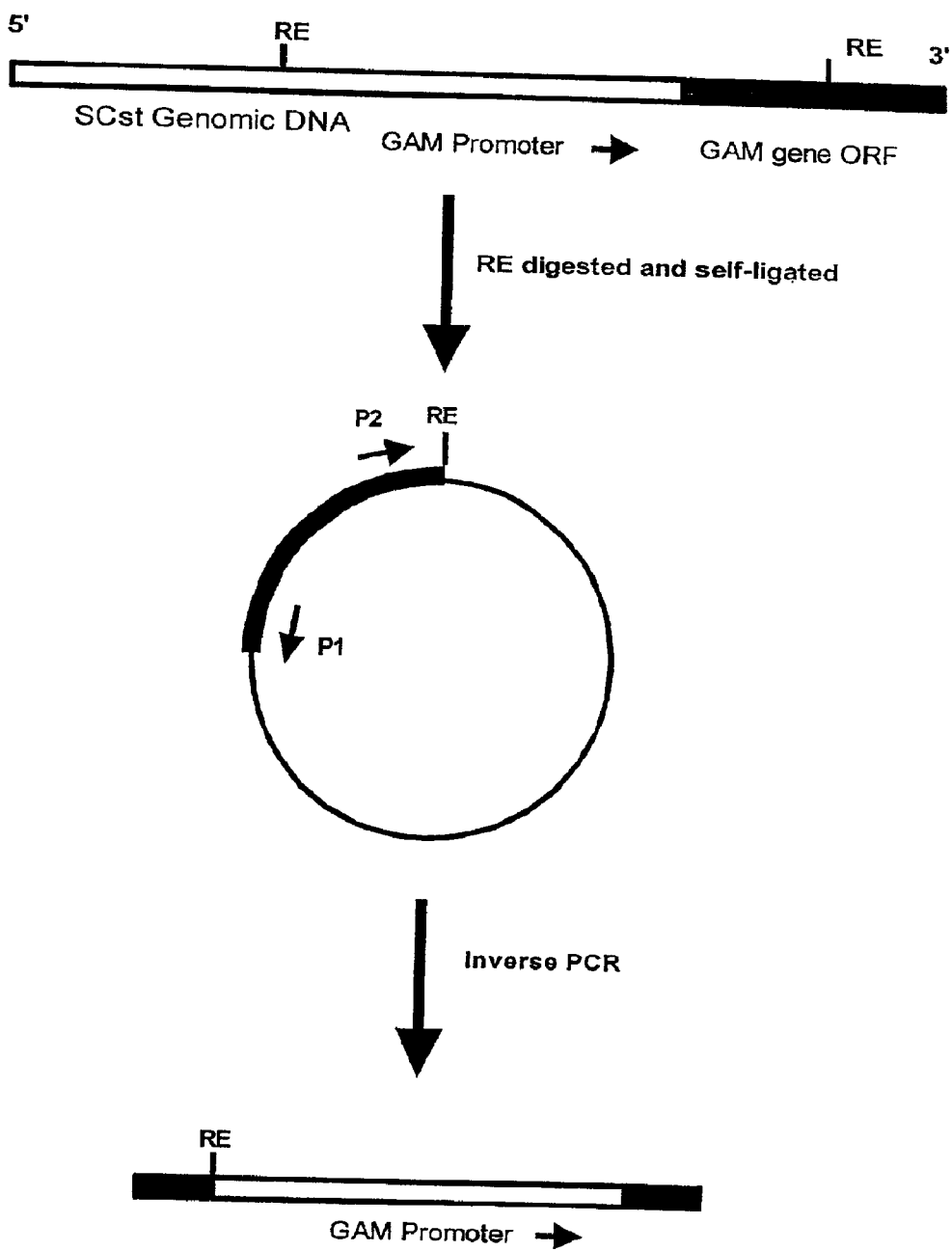
FIG. 1 is a schematic illustration depicting an inverse PCR method for promoter clone isolation.

The present invention comprises a promoter discovered in a starch utilizing yeast strain, *Schwanniomyces castellii* (ATCC 26077), which can completely hydrolyze and use starch in less than 10 hours. The novel promoter is related to an amylolytic enzyme, glucoamylase. The isolated glucoamylase promoter (GAM) clone has a length of 2184 base pairs, within which 1662 base pairs are putatively determined as the promoter region based on the open reading frame analysis. Within the 600-bp upstream of the glucoamylase initiation codon, there are putatively seven CAT boxes and ten TATA boxes, which play an important role in the regulatory mechanism of the GAM promoter.

The present invention illustrates that when fused to a reporter gene, glucuronidase gene (gus), the GAM promoter can regulate glucuronidase (GUS) expression in transformed *Saccharomyces* sp. The 1.0 kb GAM promoter shows stronger expression than the 1.5 kb GAM promoter in both glucose and starch culture medium. In addition, the *S. castellii* GAM promoter is an inducible promoter, which can regulate high gene expression at the presence of a starch while it can regulate minimal gene expression at the presence of glucose. The expression yield can be increased over twenty times when induced in a starch culture medium as compared to the glucose culture medium.

However, other reports showed that a glucoamylase structure gene of a similar *S. castellii* strain (ATCC 26076), which is under the control of a native GAM promoter, was unable to express in the transformed *Saccharomyces cerevisiae* host while this glucoamylase gene was able to express under the control of *S. cerevisiae* promoters such as galactokinase (GAL1) promoter. This is probably due to the difference in the 5' flanking region of the glucoamylase gene of these two *S. castellii* strains. When compared to the GAM gene 5' end region of a *S. castellii* strain (ATCC 26076), it was found that there are sequence differences at positions 160–162 bps, 168–169 bps, and 288 bp using GAM76 SEQ ID NO:10, as basis as shown in FIG. 5, where GAM76 stands for the GAM 5' end flanking region of *S. castellii* (ATCC 26076) and GAM77 for the GAM 5' end flanking region of *S. castellii* (ATCC 26077). In GAM77 SEQ ID NO:9, there is a sequence for CCATTATGGAT as compared to the difference of CATATGGTA in GAM76, which might cause inactivation of GAM76 in *S. cerevisiae*. However, there was no comparison made beyond 325 bps upstream of the initiation codon between two glucoamylase genes since the 5' end sequence beyond 325 bps upstream is not available for *S. castellii* (ATCC 26076).

The inducibility of the present GAM promoter provides an opportunity to regulate native or foreign gene expression in native or heterologous host strains with an inexpensive inducing agent, starch. Industrial fermentation/culture process can then use this cost-effective regulatory mechanism for certain type of metabolic pathway controlling and foreign protein accumulation.

For a clear and concise understanding of the specification and claims, including the scope given to such terms, the following definitions are provided:

PROMOTER: The expression of a gene is directed by a promoter, which is a DNA sequence and locates in the 5' region of a gene. A yeast promoter is a promoter sequence that will direct the transcription of a gene in yeast cells.

CONSTITUTIVE PROMOTER: The rate of gene transcription under such promoter is not regulated by an inducing agent, which can be a chemical compound, or a carbohydrate.

INDUCIBLE PROMOTER: The rate of gene transcription under such promoter is regulated by an inducing agent, which can be a chemical compound, or a carbohydrate.

PLASMID VECTOR: A DNA plasmid vector contains a replicon or an origin of replication able to autonomously replicate the plasmid DNA in the original host organism. A plasmid vector can also serve as both a cloning vector for DNA manipulation in a bacterial host and a shuttle plasmid vector for interested DNA expression in another host cell.

CLONING PLASMID VECTOR: Cloning vectors typically contain one or a small number of restriction endonuclease recognition sites at which interested DNA sequences can be inserted for DNA manipulation purposes. Cloning vectors also contain a marker gene that is suitable for use in the identification and selection of cells transformed with the cloning vector. Marker genes typically include genes that provide phleomycin resistance or ampicillin resistance.

EXAMPLE 1

PCR Cloning of Glucoamylase Promoter of S. Castellii

To isolate the glucoamylase promoter, S. castellii cells were grown overnight in a culture medium containing yeast extract 1%, peptone 2%, and glucose 2%. Cells were then harvested and genomic DNA was isolated and purified from the culture using the spheroplasting method. Inverse PCR method was used to clone out the promoter region, as shown in FIG. 1 where P1 is PCR reverse primer 1; P2 PCR forwarding primer 2; RE restriction enzyme site which can be cleaved both upstream of the glucoamylase (GAM) promoter and inside of the GAM gene; SCst S. castellii. PCR primers for the inverse PCR were designed based on the open reading frame of the GAM gene sequence of S. castellii. A 5' end over-hung sequence (italics) was designed to adapt restriction enzyme sites (underlined) such as Xba I and Sph I. The inverse PCR primers are listed as following:

```
Reverse primer GL1-C61:SEQ ID NO:1
5'-GC TCTAGA CAT ATG AGT AGT TTC CGT AGT AAT TGA-3'

Reverse primer GL2-C62:SEQ ID NO:2
5'-GC TCTAGA ATT ACT ATA CTT TTA ATC AGC TTC AGA-3'

Forwarding primer GL1-N64:SEQ ID NO:3
5'-GAT GCATGC TAT CTT TAA TGA CTC TGC TGT CGA TGC-3'

Forwarding Primer GL3-N66:SEQ ID NO:4
5'-GAT GCATGC TAG TTG TTA AAC CAC TGG TGG AAG GTG-3'
```

Inverse PCR method was used to isolate the promoter region. In this method, the genomic DNA was first digested with different restriction enzymes, such as Bcl I, BstB I, Hinc II, Hpa I, Sac I, and Xmn I, which locate within the 5' end of the glucoamylase gene region. Upon digestion, the DNA samples were purified and self-ligated using T4 DNA ligase, and the promoter region was subsequently cloned out by the inverse PCR reaction. Table 1 shows the reverse PCR reaction matrix, which pairs various sets of reverse primer and forwarding primer together.

TABLE 1

Inverse PCR primer pairing conditions for each digested and ligated genomic DNA samples.

| PCR reaction No. | Restriction enzyme used before ligation | Inverse PCR primer pairing |
| --- | --- | --- |
| 1 | Bcl I | GL1-C61; GL3-N66 |
| 2 | Bcl I | GL1-C62; GL3-N66 |
| 3 | BstB I | GL1-C61; GL3-N64 |
| 4 | BstB I | GL1-C62; GL3-N66 |
| 5 | Hinc II | GL1-C61; GL3-N66 |
| 6 | Hinc II | GL1-C62; GL3-N66 |
| 7 | Hpa I | GL1-C61; GL3-N66 |
| 8 | Hpa I | GL1-C62; GL3-N66 |
| 9 | Sac I | GL1-C61; GL3-N66 |
| 10 | Xmn I | GL1-C61; GL3-N66 |
| 11 | Xmn I | GL1-C62; GL3-N66 |

Figure 2:
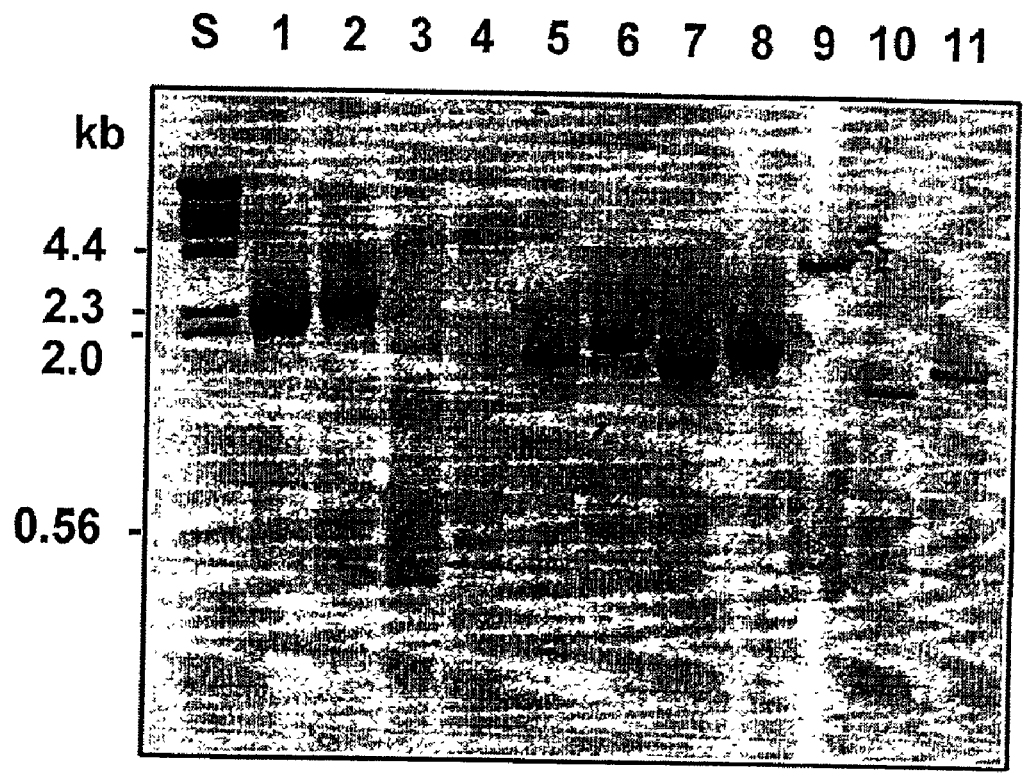
FIG. 2 is a photograph of a reverse gel image of PCR clones of *S. castellii* glucoamylase promoter.

The inverse PCR reactions were conducted based on the primer pairing outlined in Table 1. After PCR reaction, the PCR products were separated in an agarose gel by electrophoresis. The inverse PCR results are shown in a reverse gel image in FIG. 2, where lane number is correspondent to each inverse PCR reaction in Table 1 and lane S is the Hλ DNA size marker. The isolated GAM promoter clones are shown as dark bands in the gel picture. Lanes 1, 2, 5, 6, 7, and 8 show strong bands, which correspondent to the ligated DNA samples previously cleaved by Bcl I, Hinc II, and Hpa I, respectively. The sizes of the PCR clones range from about 0.4 kb to 4.4 kb, and the strong bands range from about 1.7 kb to 2.3 kb.

EXAMPLE 2

Nucleotide Sequence of GAM Promoter Sequence

Figure 3:
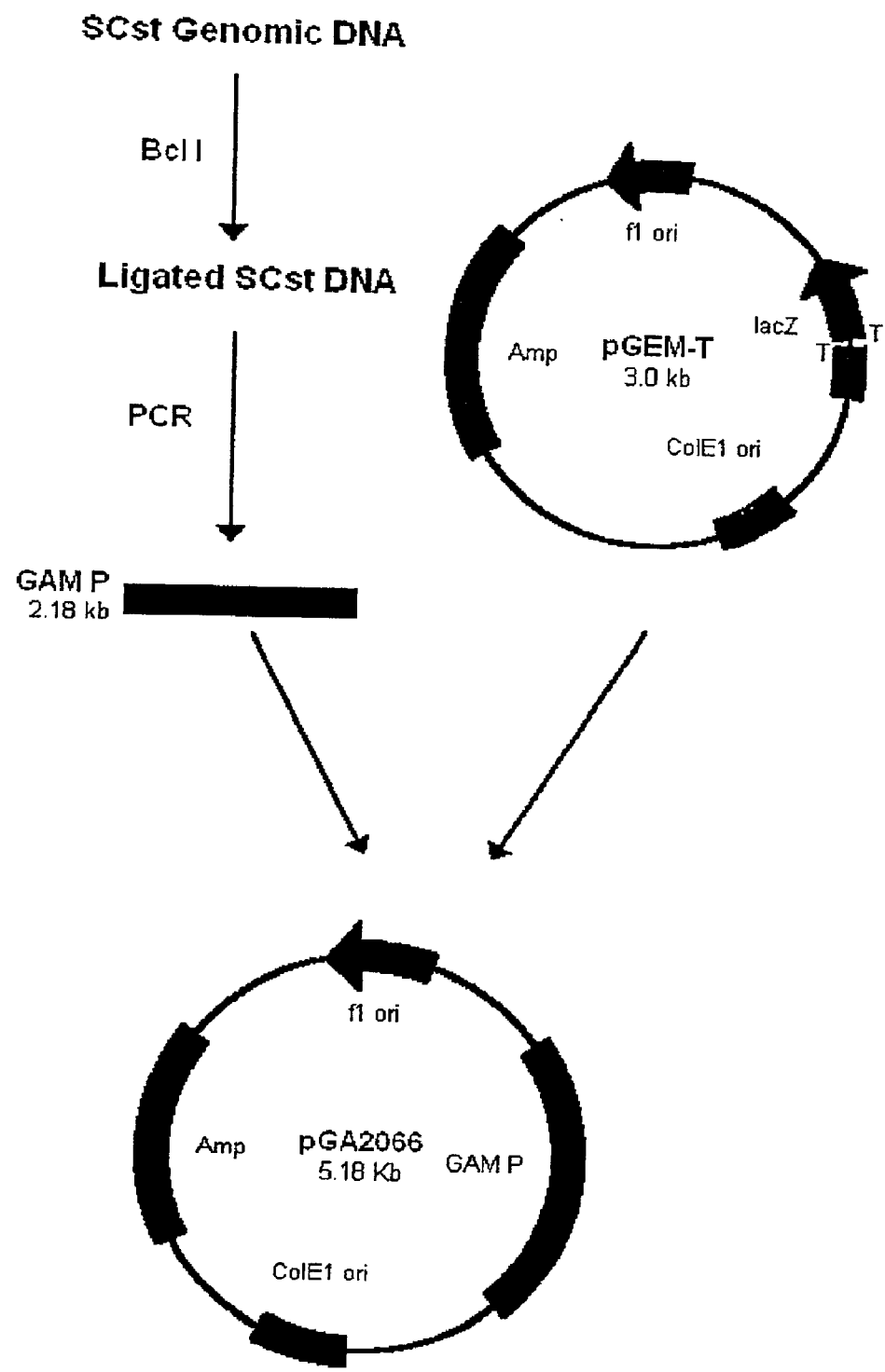
FIG. 3 is a schematic illustrating the construction of a plasmid vector pGA2066.

PCR product No. 2 contains sufficient length (about 2.3 kb) of the GAM gene upstream sequence and the initial codon ATG of the GAM gene. The GAM promoter clone No. 2 was cloned into a unique cloning site containing 3' terminal thymidine (T) to both ends of a cloning plasmid vector pGEM-T (Promega, Madison, Wis.) to form pGA2066, as shown in FIG. 3, where Amp is the ampicillin resistance gene; ColE1 is the origin for plasmid replication during gene manipulation in E. coli strains; f1 ori is the phage origin. Individual colonies were picked to confirm DNA insertion. Two of the randomly picked individual clones, pGA2066-21 and pGA2066-29, were sequenced to compare the identity of these two clones. The results showed that these two clones have the same sequences. In addition, other clones from PCR products No. 8 and 11 were also sequenced and they had the identical sequences as that of No. 2, and the sequence downstream of the initiation codon ATG is identical to the GAM1 gene. Therefore, the upstream of clone No. 2 has the GAM promoter region. Clone No. 2 in pGA2066-21 was chosen and completely sequenced from both ends, and has a length of 2182 bp, corresponding to SEQ ID NO:8, as shown in FIG. 4. The putative TATA box and CAT box are bold and underlined. There are seven CAT boxes and ten TATA boxes within 600 base pairs upstream of the initial codon. In addition, the open reading frame analysis indicates that the GAM promoter sequence locates between 485 bp to 2148 bp, between which there are 1662 bps for the GAM promoter and there is no long open reading frame.

EXAMPLE 3

Vector Construction for GAM Promoter Analysis

Figure 6:
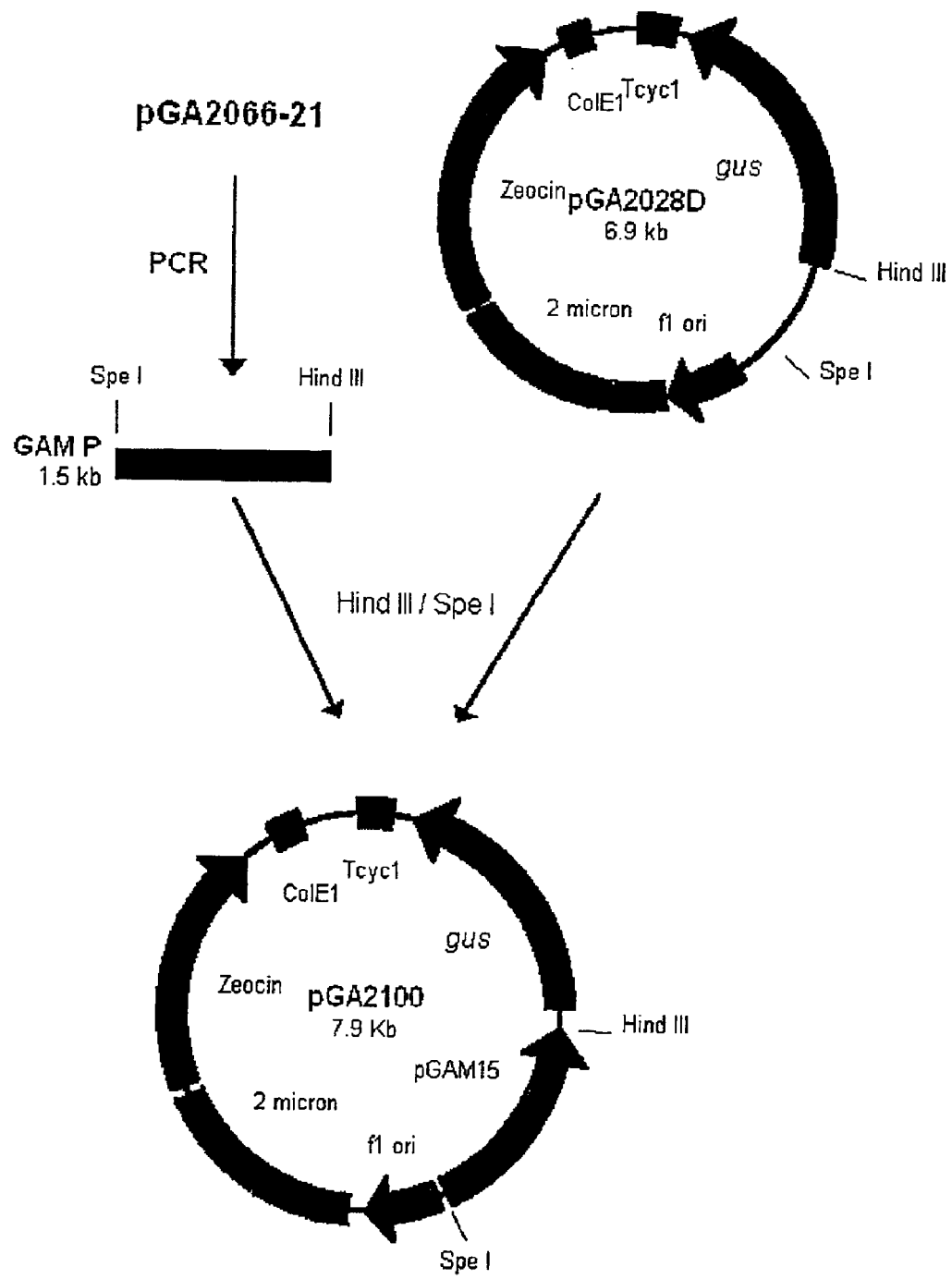
FIG. 6 is a schematic illustrating the construction of a plasmid vector pGA2100.

To test the activity of the glucoamylase (GAM) promoter, a bacterial glucuronidase gene was fused to the 1.5 kb and 1.0 kb glucoamylase promoters. An episomal yeast plasmid vector pGA2028D was used, as shown in FIG. 6. The GAM promoter was cloned out from pGA2066-21, forming the 1.5 kb and 1.0 kb GAM promoters (GAM15 and GAM10). A 5' end over-hung sequence (italics) was designed to adapt restriction enzyme sites (underlined) such as Spe I at the 5' end and Hind III at the 3' end, using the following primers, respectively.

```
Forwarding primer GM15-N for 1.5 kb GAM promoter:
                                            SEQ ID NO:5
5'-TCT AGA ACTAGT GAT TTC TGA TTG ATT TGA GTT-3'

Forwarding primer GM10-N for 1.0 kb GAM promoter:
                                            SEQ ID NO:6
5'-TCT AGA ACTAGT TCT ATC AAA CTA CTC CAA ATA-3'

Reverse primer GM-C for both GAM promoters:
                                            SEQ ID NO:7
5'-GGT ACC AAGCTT CTT GCT TGT TAT AAT ACA GTC-3'
```

Figure 7:
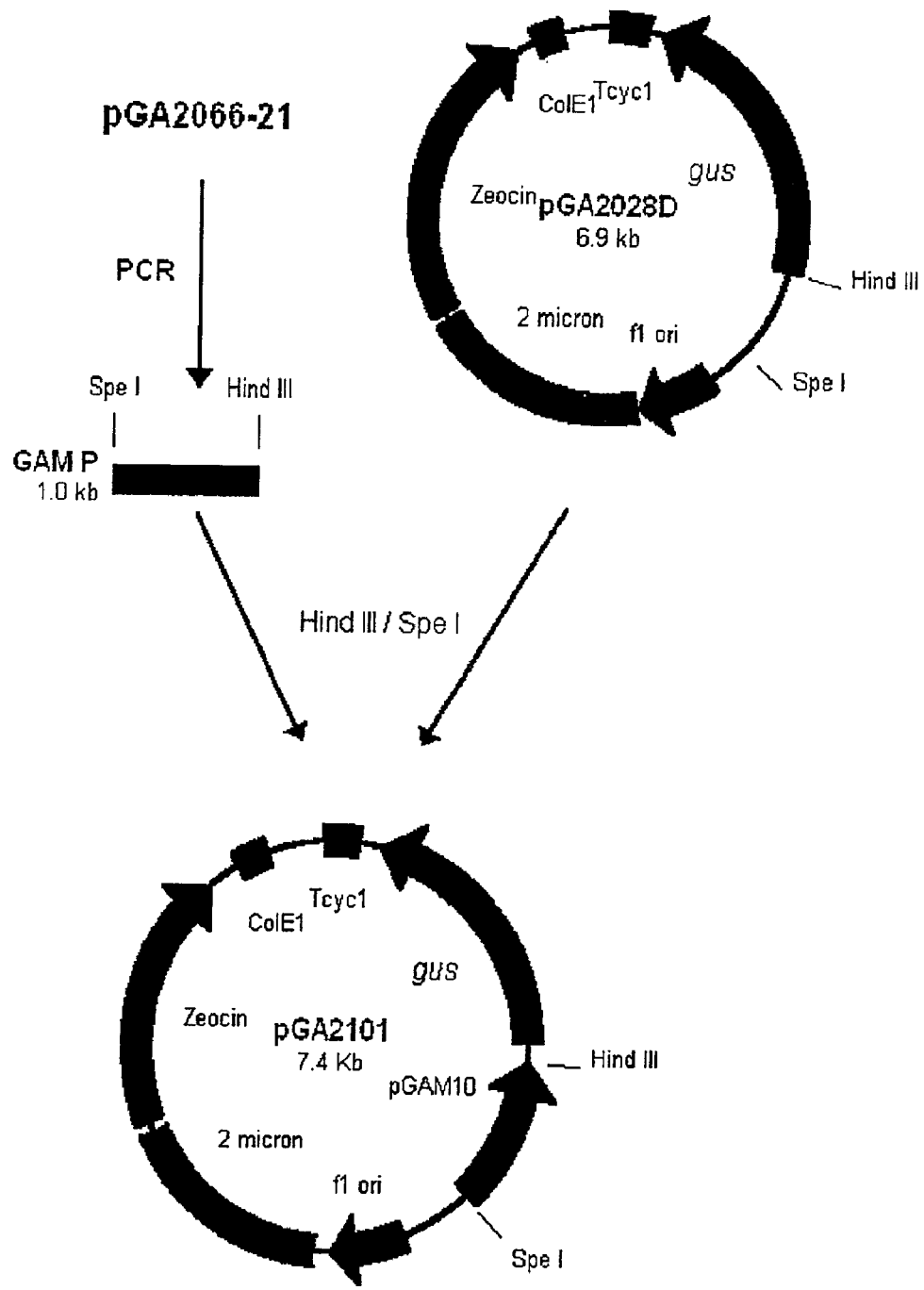
FIG. 7 is a schematic illustrating the construction of a plasmid vector pGA2101.

FIG. 6 shows the constructed vector pGA2100 containing the 1.5 kb GAM promoter, and FIG. 7 shows the vector pGA2101 containing the 1.0 kb GAM promoter, where 2 micron is a DNA replicon for plasmid replication in *Saccharomyces* strains; ColE1 is the origin for plasmid replication during gene manipulation in *E. coli* strains; f1 ori is the phage origin; gus is the bacterial glucuronidase gene; Tcyc1 is the transcription terminator; and Zeocin is the Zeocin resistance gene (Invitrogen, Inc. Carlsbad, Calif.). pGAM15 and pGAM10 stand for the GAM promoter with lengths of 1.5 kb and 1.0 kb, respectively.

EXAMPLE 4

Glucuronidase (GUS) Expression Regulated by GAM Promoter in Glucose Culture Medium A starch-degrading *Saccharomyces* hybrid yeast strain, obtained from James R. Mattoon of University of Colorado, was used as the host for plasmid transformation and promoter activity testing. A transformation kit (Invitrogen, Inc., Carlsbad, Calif.) was used for preparing competent yeast cells, which were subsequently used for the transformation of pGA2100 and pGA2101. After transformation, cells were plated onto YPD agar medium plate containing glucose 2%, yeast extract 1%, peptone 2%, and antibiotic Zeocin (Invitrogen, Inc., Carlsbad, Calif.). After four-day incubation at 30° C., transformed yeast colonies were obtained on the selective culture plate and used for the GUS activity analysis.

Colonies were picked and intracellular protein samples were extracted using the glass-bead disintegrating method. Briefly, in this method single transformed colony was suspended in 300 μl of extraction buffer containing 50 mM sodium phosphate at a pH 7.0, 1 mM EDTA, 1 mM phenylmethylsulfonyl fluoride (PMSF), 10 mM beta-mercaptoethanol, and 0.1% triton X-100. The cells were then disrupted by acid-washed glass beads (average diameter 100 μm) on a vortexer. After cell disruption, the sample was centrifuged at 20,000×g for 5 minutes. The supernatant was saved for both protein and GUS activity assays. Protein was determined using a BioRad protein assay reagent (Bio-Rad Laboratories, Hercules, Calif.) and glucuronidase activity using an enzymatic reaction in which a substrate 4-methylumbelliferul-beta-D-glucuronide (MUG) can be hydrolyzed by glucuronidase to a fluorescent compound 4-methylumbelliferone. One unit of glucuronidase activity is defined as the amount of glucuronidase that produces one pmole of 4-methyl umbelliferyl (MU) from MUG per minute at 37° C. The specific activity of glucuronidase is calculated as the units of glucuronidase per milligram of total protein.

After transformation, positive yeast colonies were selected and grown in YPD plates containing glucose as the main carbon source and an antibiotic Zeocin. Transformed colonies were harvested and protein samples were prepared. Table 2 shows the results of glucuronidase specific activities of both clones transformed with pGA2100 and pGA2101, respectively. Two transformants are under the control of the GAM15 promoter, and four transformants are under the control of the GAM10 promoter. It is evident that GUS activity is detected in all the tested clones, but not in the none-transformed control cell, indicating that the isolated glucoamylase promoter is active in the heterologous host, *Saccharomyces* sp. The GUS expression under GAM10 promoter is higher than the one under the control of GAM15 promoter.

TABLE 2

GUS activity in transformed *Saccharomyces* sp. colonies grown in medium containing glucose 2%, yeast extract 1%, and peptone 2%.

| Clone No. | Promoter | GUS specific activity (unit/mg) | Average activity (Unit/mg) |
|---|---|---|---|
| C* | — | 6 | 6 |
| 1 | GAM15 | 54 | 60 |
| 2 | | 66 | |
| 3 | GAM10 | 100 | 97 ± 15 |
| 4 | | 99 | |
| 5 | | 111 | |
| 6 | | 76 | |

*Host cell without transformation of GUS expression vector

EXAMPLE 5

Glucuronidase Expression Regulated by GAM Promoter in Starch Culture Medium The GUS expression under glucoamylase promoter exhibits lower activity as shown in Table 2 when the culture medium contains glucose as the primary carbon source. In this test, transformed colonies were first grown in the medium contain glucose. After washing, cells were transferred into culture medium containing potato starch 2%, yeast extract 1%, and peptone 2% for GUS the expression tests. Results are shown in Table 3. After a 15-hour growth period in the starch medium, intracellular protein samples were obtained using the glass-bead disintegrating method and GUS activity was determined. GUS activity was detected in all transformed cultures. The highest GUS activity was 1405 U/mg-protein under the control of the GAM15 promoter, and 2123 U/mg-protein under the control of GAM10 promoter. When induced by starch at its highest expression level, the transformed GUS activity is as about 23-fold as the activity in the glucose medium for the GAM15 promoter, and as about 22-fold as the activity in the glucose medium for the GAM10 promoter. These results indicate that the glucoamylase promoter is highly induced by starch, which can be used as an inexpensive inducting agent for gene expression regulation.

TABLE 3

GUS activity in transformed *Saccharomyces* sp. colonies grown in medium containing potato starch 2%, yeast extract 1%, and peptone 2%.

| Clone No. | Promoter | GUS specific activity (unit/mg) | Average activity (Unit/mg) |
|---|---|---|---|
| C* | — | 0.0 | 0.0 |
| 1 | GA15 | 1394 | 980 ± 350 |
| 2 | | 1405 | |
| 3 | | 582 | |
| 4 | | 854 | |
| 5 | | 685 | |
| 6 | | 963 | |
| 7 | GA10 | 1398 | 1521 ± 327 |
| 8 | | 1645 | |
| 9 | | 2123 | |
| 10 | | 1250 | |
| 11 | | 1432 | |
| 12 | | 1277 | |

*Host cell without transformation of GUS expression vector

EXAMPLE 6

Glucuronidase Expression Regulated by Glucoamylase Promoter in Plant Cells

To test functionality of glucoamylase promoter in plant cell cultures, the constructed plasmid vectors pGA2100 and pGA2101 were used in a transient assay using plant cell protoplasting method. A 3-day old *Nicotiana tabacum* cell suspension was used for the preparation of protoplasts. Briefly, protoplasts were isolated by treating the suspension cells with a pH 5.8 solution containing 10 mg/l cellulase, 500 µg/ml pectolyase (Kanematsu-Gosho, Los angeles, Calif.) and 0.4 M D-mannitol at 28° C. for 20 minutes with a gentle shaking at 100 rpm. The protoplasts were then extensively washed with 0.4 M mannitol to remove cellulase and pectolyase. Finally, $1 \times 10^6$ protoplasts were resuspended in 0.5 ml of pH 5.5 electroporation buffer containing 2.38 mg/ml HEPES, 8.76 mg ml NaCl, 735 µg/ml CaCl2 and 0.4 M D-mannitol.

After addition of 20 µg superecoil plasmid DNA of pGA2100 and pGA2101, respectively, and 10 µg salmon sperm DNA as a carrier DNA, the protoplasts were them electroporated at a 300 volt pulse with 210 µF capacitor. The treated protoplasts were subsequently transferred in 7 ml of protoplast culture medium in a Petri dish and cultured for 48 hours at 28° C. The culture medium is a modified Murashige and Skoog (MS) medium (Murashige and Skoog, 1962) containing 4.3 mg/ml MS salt supplemented with 3% sucrose, 0.18 mg/ml $KH_2PO_4$, 0.1 mg/ml inositol, 1 µg/ml thiamine hydrochloride, and 0.2 µg/ml 2.4-dichlorophenoxyacetic acid (2.4-D), and 0.4 M D-mannitol.

The culture protoplasts were collected by gentle centrifugation and suspended in 100 µl extraction buffer containing 50 mM Tris-HCl pH 8.3, 227 mM NaCl, 1 mg/ml bovine serum albumin, and 1 mg/ml sodium azide. Protein samples were extracted by sonicating the protoplasts three times for 8 seconds with 30-second intervals. The protein samples were harvested by centrifuging the sonicated mixture at 15,000 g for 5 minutes. The supernatant was saved and protein concentration was measured by the Bio-Rad Protein Assay method (Bio-Rad, Hercules, Calif.). The glucuronidase activities were assayed using the same method as described in example 4. The glucuronidase activity results are shown in the following table. The results indicate that *S. castellii* glucoamylase promoter can regulate the expression of glucuronidase in plant cells.

TABLE 4

GUS activity in electroporated *Nicotiana tabacum* cells.

| Test No. | Promoter | Culture Medium | GUS Specific Activity (unit/mg) |
|---|---|---|---|
| Control* | — | Sucrose | 10.2 |
| 1 | GA15 | Sucrose | 49.2 |
| 2 | | | 36.0 |
| 3 | GA10 | Sucrose | 60.0 |
| 4 | | | 51.2 |

*Host cell without transformation of glucuronidase expression vector.

We claim:

1. A method of regulating expression of a gene product comprising the steps of:
   a. providing a coding region that encodes a gene product;
   b. fusing the coding region with an isolated yeast promoter to form a fused promoter/coding region; wherein the promoter comprises at least nucleotides 486 through 2147 of SEQ ID NO.:8; and
   c. integrating the fused promoter/coding region within a yeast genomic DNA such that the promoter regulates the expression of the gene product.

2. The method of claim 1 wherein the genomic DNA is from a species of yeast other than *Schwanniomyces castellii*.

3. An isolated gene promoter comprising at least nucleotides 486 through 2147 of SEQ ID NO.:8.

4. A vector comprising the isolated promoter of claim 3.

5. The vector of claim 4 wherein the vector is a plasmid vector.

6. A chimeric gene comprising;
   the isolated promoter of claim 3; and
   a nucleotide sequence encoding a gene product other than the *Schwanniomyces castellii* glucoamylase gene product, wherein the isolated promoter is fused in transcriptional controlling relation to the nucleotide sequence encoding the gene product.

7. A method of expressing a gene product comprising:
   providing a starch inducible promoter comprising at least nucleotides 486 through 2147 of SEQ ID NO.:8;
   fusing the starch inducible promoter to a coding DNA sequence to form a chimeric gene, wherein the coding sequence encodes a product of interest;
   introducing the chimeric gene into a host cell;
   providing a growth medium; and
   inducing expression of the chimeric gene by providing starch to the growth medium.

8. The method of claim 7 wherein the starch is the primary carbon source in the growth medium.

9. The method of claim 7 wherein the product of interest is glucuronidase.

10. A method of expressing a gene product comprising:
    providing a host cell;
    introducing a DNA construct into the host cell, the construct comprising a nucleotide coding sequence that encodes a gene product operably linked to a promoter comprising at least nucleotides 486 through 2147 of SEQ ID NO.:8; and
    expressing the gene product within the host cell.

11. The method of claim 10 wherein the host cell is a plant cell.

12. The method of claim 10 wherein the host cell is a plant protoplast.

13. The method of claim 10 wherein the host cell is a *Nicotinia tabacum* cell.

14. The method of claim 10 wherein the gene product is an enzyme.

15. A host cell comprising a promoter operably linked to a coding sequence encoding a gene product other than the *Schwanniomyces castellii* glucoamylase gene product, the promoter comprising at least nucleotides 486 through 2147 of SEQ ID NO.:8.

16. The host cell of claim 15 wherein the host cell is a plant cell.

* * * * *

SEQUENCE LISTING

<160> NUMBER OF SEQ ID NOS: 10

<210> SEQ ID NO 1
<211> LENGTH: 35
<212> TYPE: DNA
<213> ORGANISM: Artificial Sequence
<220> FEATURE:
<223> OTHER INFORMATION: oligonuceotide primer

<400> SEQUENCE: 1
gctctagaca tatgatgagt ttccgtagta attga      35

<210> SEQ ID NO 2
<211> LENGTH: 35
<212> TYPE: DNA
<213> ORGANISM: Artificial sequence
<220> FEATURE:
<223> OTHER INFORMATION: oligonucleotide primer

```
<400> SEQUENCE: 2
gctctagaat tactatactt ttaatcagct tcaga                        35

<210> SEQ ID NO 3
<211> LENGTH: 36
<212> TYPE: DNA
<213> ORGANISM: Artificial sequence
<220> FEATURE:
<223> OTHER INFORMATION: oligonucleotide primer

<400> SEQUENCE: 3
gatgcatgct atctttaatg actctgctgt cgatgc                       36

<210> SEQ ID NO 4
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 4
gatgcatgct agttgttaaa ccactggtgg aagtg                        36

<210> SEQ ID NO 5
<211> LENGTH: 33
<212> TYPE: DNA
<213> ORGANISM: Artificial sequence
<220> FEATURE:
<223> OTHER INFORMATION: oligonucleotide primer

<400> SEQUENCE: 5
tctagaacta gtgatttctg attgatttga gtt                          33

<210> SEQ ID NO 6
<211> LENGTH: 33
<212> TYPE: DNA
<213> ORGANISM: Artificial sequence
<220> FEATURE:
<223> OTHER INFORMATION: oligonucleotide primer

<400> SEQUENCE: 6
tctagaacta gttctatcaa actactccaa ata                          33

<210> SEQ ID NO 7
<211> LENGTH: 33
<212> TYPE: DNA
<213> ORGANISM: Artificial sequence
<220> FEATURE:
<223> OTHER INFORMATION: oligonucleotide primer

<400> SEQUENCE: 7
ggtaccaagc ttcttgcttg ttataataca gtc                          33

<210> SEQ ID NO 8
<211> LENGTH: 2182
<212> TYPE: DNA
<213> ORGANISM: Schwanniomyces castellii

<400> SEQUENCE: 8
tgatcatctt gaagttaaat ccaagttatt caagtaattt aaagttgaat aatgtagtta    60
tttcagtggc cttaaaccag tccatcgaga cgacttcagc ctcttcgaga ccacaaggtt   120
cgtttaataa ggaaatgaat agaatcacct ggagatattc gcagccatta atactatcaa   180
```

-continued

```
gtgaaaatcc tgaagaaaaa ttaattgcaa gattttgac taatagtaaa ggtagtgaac      240
atgaaagtgg tattcaagtt aaattttga ttaatgatcc tccactgaaa ttttctaagg      300
ctttatattt tgatgatgaa tcaacagagg ttccttgtgt aaggaatctt attagtggaa      360
gctacagcag tcattcttaa acatgattaa tgtctagatt tattggttat ttaggcattc      420 tttttttaa aatattttt gttaatatct ttgagtttat gttttttgtt cgttttatct       480
tttaaagtag tgtttatagt tttagtattg ttaaccttt ttcctaaat gttagtatgc       540 atgcttaaaa tgatgtcaga ggtagagtat gaattaattc cttttataaa tgctgttttg      600
tgagatcttt taaaattatc tatctttctc tttaaaggat atgttttgat ttctgattga      660
tttgagttcc aacgacaatc gaatgtattc atatagtagt tactacctta aacacaatcc      720
agatggttta accaactgat gcctaagttt catgtggtgc tctttaacat ccttttgtc       780 ttcaaatttc aatgccatta gttcacatgt atatacgcca agagagtttt gtgaccaact      840
tacatttact agcaagtatt atctacaaag caaaaattac gacatatttg tgttggatcc      900
atcaactgtg gacacgaata acaagttccc aggattccta attattcaac tgccagataa      960
ataacatata tccaaaggtt caacattatt taccaaattc aaagttggat tttgttaaat      1020
ggaatgacaa tagaaattgg ttgggtttat gtgcaaaaga atctaatttt gcatatattt      1080
tcgtaaactt caattcctaa aatcttgcga aacttctctt tagaggaaat tggttccatt      1140
ctaccttcta tcaaactact ccaaatacaa gcggcttaaa atctacatgt aaataccta      1200 ctgttacaat tattctccct tgaattgacc aacctgacca tgaaaccttt ttggaatcag      1260
cctatttaca ctaataattt ttatcctaag tgccatggaa gctattatat aagttttacc      1320
agtgagagag gatcttgact tgacgaacaa catttcaact agaatgctct atatcttcct      1380
ccgggaaaag cggccgctac catttgtttt acactctcac catcacaaaa gtgccattca      1440 acggatttt gtccgcgatc tctcggtaaa atgtgttctc gaaatgtgcc ttattgccaa       1500
aaaataaaaa ataaaaaata atgtgggggt ggcatccttc aacttgtcgg atttattgcg      1560
taatagattt caatcaacat gatcttaatc catactggct tatgctctct tagaggctta      1620
tctcttaata atttattat atatctattc taactattga aaaactattg aatatgcttt       1680
aaaactggct atgctgtatt tgacttctca atgcaaaatt caacacttct ataatgtaac      1740
acactaaaaa ttttcagaa tcggaatagt cgagacaatt gatttccga actattgcga       1800 aatccaatgg agcaacaatg agagatctac attttaaacc ccagtctact ccagatattg      1860
gagtataacc ccattcttac cgttatatcc atgacccgca tcgaaattt caaaggattt      1920 cgaggaaatt ctttcctaaa atacgaagtg ttattggtga ttcaattact acggaaacta     1980
ctccattatg gatgtagagt tggtgaatgt agcgcaattg taatttgcga agttatagta     2040
atagtttggc aaactggaga attttttcatt attgggaaaa tataaataaa ggcaagtatc    2100
cattgaaatt ttaaaaatga actcatgact gtattataac aagcaagatg attttctga     2160 agctgattaa aagtatagta at                                              2182
```

<210> SEQ ID NO 9
<211> LENGTH: 328
<212> TYPE: DNA
<213> ORGANISM: Schwanniomyces castellii

<400> SEQUENCE: 9

```
agatctacat tttaaacccc agtctactcc agatattgga gtataacccc attcttaccg      60
ttatatccat gacccgcatc gaaattttca aaggatttcg aggaaattct ttcctaaaat     120
```

-continued

```
acgaagtgtt attggtgatt caattactac ggaaactact ccattatgga tgtagagttg      180
gtgaatgtag cgcaattgta atttgcgaag ttatagtaat agtttggcaa actggagaat      240
ttttcattat tgggaaaata taaataaagg caagtatcca ttgaaatttt aaaaatgaac      300
tcatgactgt attataacaa gcaagatg                                         328

<210> SEQ ID NO 10
<211> LENGTH: 325
<212> TYPE: DNA
<213> ORGANISM: Schwanniomyces castellii

<400> SEQUENCE: 10
agatctacat tttaaacccc agtctactcc agatattgga gtataacccc attcttaccg       60
ttatatccat gacccgcatc gaaattttca aaggatttcg aggaaattct ttcctaaaat      120
acgaagtgtt attggtgatt caattactac ggaaactact catatggtag tagagttggt      180
gaatgtagcg caattgtaat ttgcgaagtt atagtaatag tttggcaaac tggagaattt      240
ttcattattg ggaaaatata aataaaggca agtatccatt gaaattttaa aatgaactca      300
tgactgtatt ataacaagca agatg                                            325
```